United States Patent [19]
Pohndorf

[11] Patent Number: 4,512,351
[45] Date of Patent: Apr. 23, 1985

[54] PERCUTANEOUS LEAD INTRODUCING SYSTEM AND METHOD

[75] Inventor: Peter J. Pohndorf, Miami Shores, Fla.

[73] Assignee: Cordis Corporation, Miami, Fla.

[21] Appl. No.: 442,964

[22] Filed: Nov. 19, 1982

[51] Int. Cl.³ .............................................. A61N 1/04
[52] U.S. Cl. .................................................... 128/786
[58] Field of Search .............. 128/753, 754, 784, 786, 128/419 R

[56] References Cited

U.S. PATENT DOCUMENTS

| | | | |
|---|---|---|---|
| 3,598,108 | 8/1971 | Jamshidi | 128/754 |
| 4,141,365 | 2/1979 | Fischell et al. | 128/419 R |
| 4,166,469 | 9/1979 | Littleford | 128/784 |
| 4,230,123 | 10/1980 | Hawkins, Jr. | 128/753 |

OTHER PUBLICATIONS

Cordis Corporation, Catalog No. 961-102, May, 1981, pp. 1-12.

Primary Examiner—William E. Kamm
Attorney, Agent, or Firm—Lockwood, Alex, Fitzgibbon & Cummings

[57] ABSTRACT

A method and apparatus for introducing a neural stimulator lead into the epidural space in the spinal cord of a patient includes an introducer into which an epidural needle assembly may be inserted through a cannula in the introducer. The introducer along with the epidural needle assembly, such as a Tuohy needle, are inserted between the vertebrae in the patient's spine so that the leading tip of the epidural needle assembly and the introducer are adjacent the epidural space. The epidural needle assembly includes a needle which also has a cannula and an obturator which is inserted in the cannula when the introducer and epidural needle assembly are being inserted between the vertebrae. The obturator is thereafter removed from the cannula of the needle, the needle cannula is filled with a saline solution, and the introducer is further advanced into the epidural space as the needle is withdrawn from the cannula of the introducer. The neural stimulator lead is then inserted through the cannula of the introducer, until it is positioned in the epidural space. Once the electrode of the lead is positioned at its desired location, the introducer is withdrawn along the lead and the introducer is split away from the electrode by a pair of handles and a weakened score line extending longitudinally of the cannula of the introducer.

20 Claims, 11 Drawing Figures

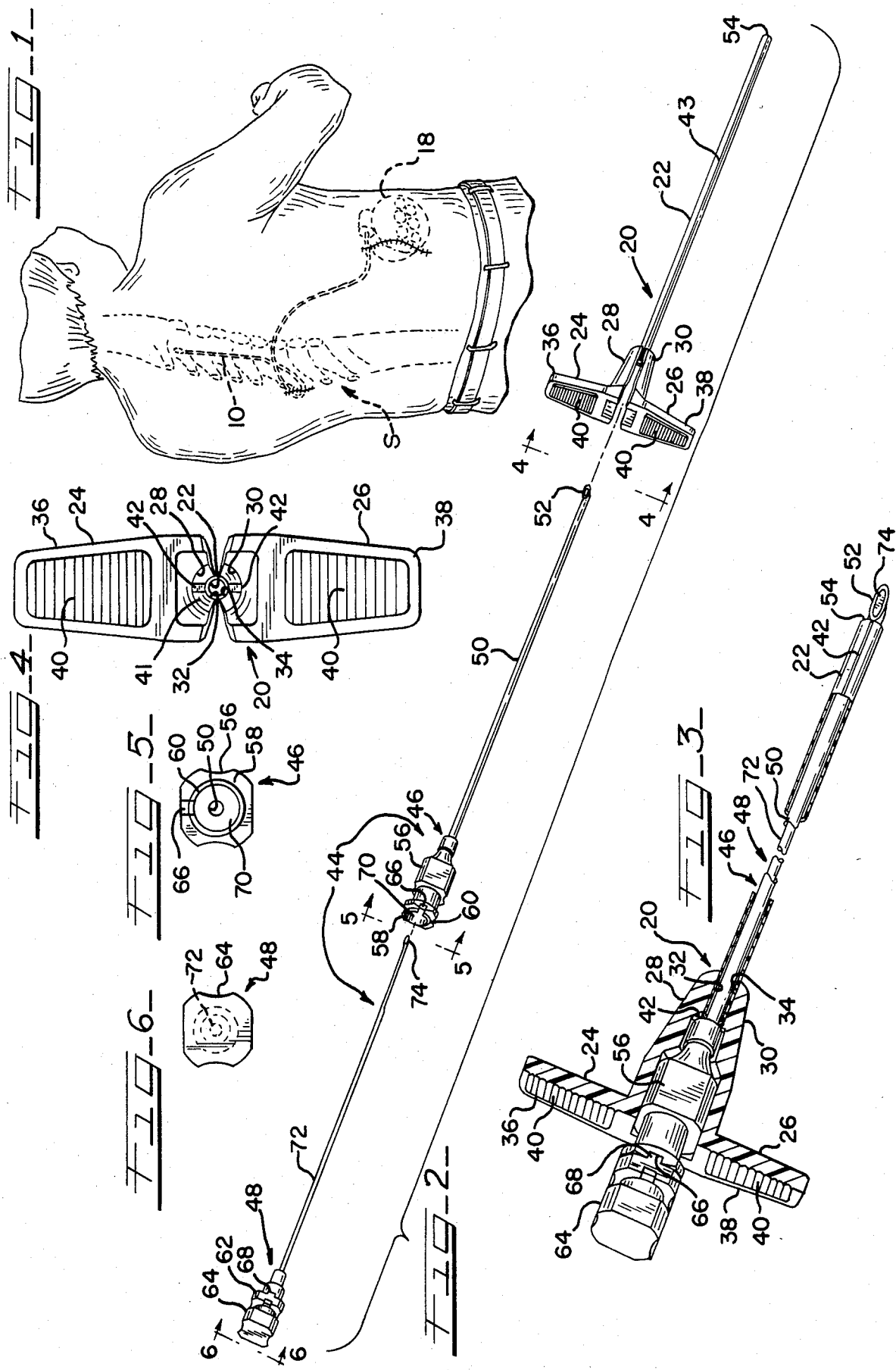

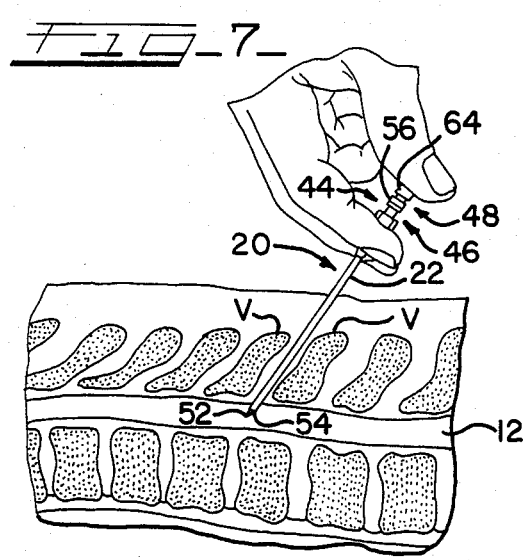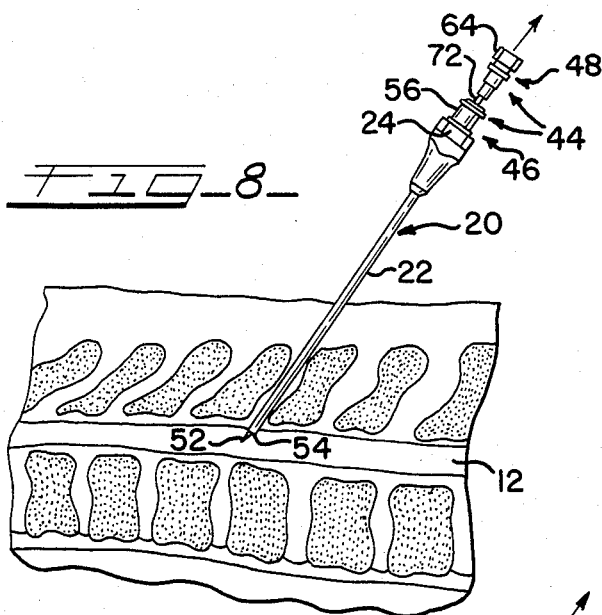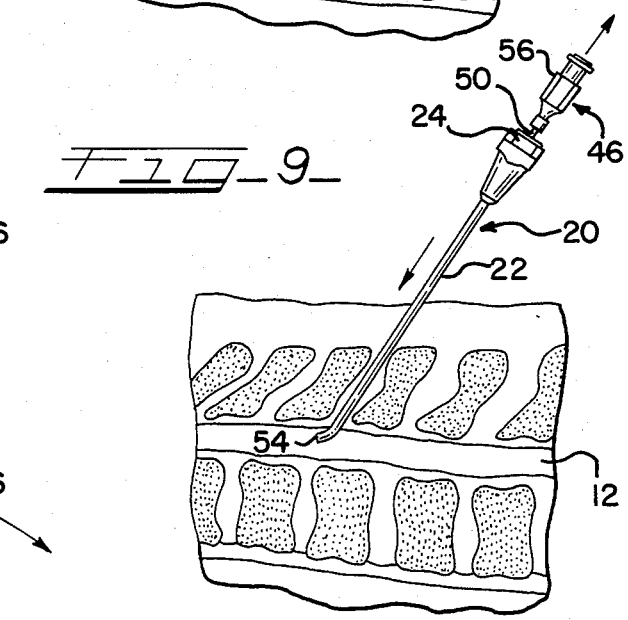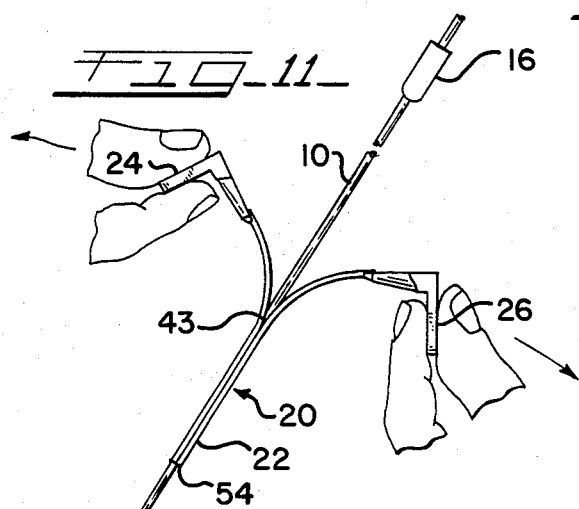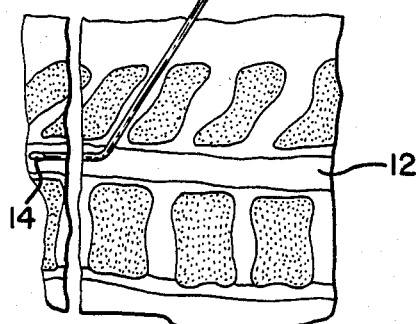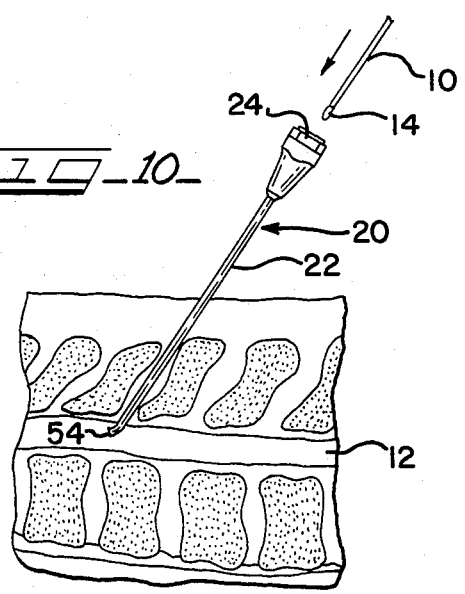

PERCUTANEOUS LEAD INTRODUCING SYSTEM AND METHOD

BACKGROUND AND SUMMARY OF THE INVENTION

The present invention relates to a method and apparatus for the introduction of a percutaneous flexible member and, more particularly, to a method and apparatus for the introduction of a flexible neural stimulator lead in the epidural space in the spinal cord of a patient.

In the past, neural stimulator leads have been implanted in the epidural space of the spinal cord of a patient for stimulating a selected location or locations along the spinal cord for such purposes as the relief of pain. Such leads have been introduced and fixed by the use of an epidural needle assembly such as, for example, a Tuohy needle. Tuohy needles typically include an elongate cannula into which an obturator is inserted. In practice, the needle cannula, with the obturator therein, is percutaneously inserted between vertebrae in the patient's spine so that the leading tip of the needle is in the patient's epidural space. Once this has been accomplished, the obturator is removed from the needle cannula and the neural stimulator lead is inserted through the cannula of the needle and into the epidural space where it is positioned and fixed at the location which is to be stimulated. Once positioning has been accomplished, the needle is withdrawn from the patient along the portion of the lead which extends from the patient's body and over the end of the lead. At this point, a terminal is formed upon or attached to the end of the lead and the terminal is electrically connected to a preferably subcutaneously implanted stimulator which generates electrical pulses or signals, as is known in the art, for the desired stimulation of the patient's spinal cord.

One difficulty which is presented in such prior method and apparatus is the fixing of the terminal to the end of the lead. It is preferable to mold or otherwise form the terminal on the end of the lead at the time of manufacture of the lead, rather than after the lead has been installed and fixed in the patient. Fixing of the terminal on the lead after fixation prolongs the procedure increasing the possibility of trauma to the patient, jeopardizes the maintenance of sterile conditions and precludes molding of the terminal directly to the lead.

The aforementioned installation and fixation procedure in which the needle cannula is ultimately withdrawn along the lead and over the end of the lead following installation and fixation precludes the mounting of a terminal at the time of manufacture which is larger in diameter than the diameter of the lead itself. This is because the diameter of the needle cannula is preferably only large enough to allow movement of the needle along the lead to withdraw the needle following lead installation. If such terminal is preattached to the lead at the time of manufacture, removal of the epidural needle assembly will be blocked. Thus, the prior methods and apparatus necessitated that the terminal at the end of the neural stimulator lead either be limited in diameter to the diameter of the lead, if the terminal was to be preattached to the lead at the time of manufacture, or required attachment following fixation of the lead. The former substantially limits the types of terminals which could be used and the latter prolongs the procedure, jeopardizes the maintenance of sterile conditions, increases the possibility of malfunction, and precludes molding of the terminal to the lead under manufacturing controlled conditions.

A method and apparatus incorporating the principles of the present invention, obviates the need for the removal of any component over the end of a neural stimulator lead after placement of the lead in the epidural space of the patient. The method and apparatus incorporating the principles of the present invention includes an introducer which is of inexpensive construction and is readily capable of manufacture, through which the lead is introduced and fixed in the epidural space of the patient. Once the lead has been introduced and fixed, the introducer may be easily withdrawn along the lead and split away from the lead before it reaches the end of the lead and the terminal. The ability to easily and quickly split the introducer away from the neural stimulator lead in the method and apparatus of the present invention enables the lead terminal, which may take a wide variety of forms, to be mounted to the lead at the time of manufacture and under assured sterile conditions, and reduces the time involved in the lead implantation procedure. Moreover, the introducer of the present invention need not be any larger in diameter than the prior needles which were previously employed in the installation of neural stimulator leads.

In one principal aspect of the present invention, a method of introducing a flexible member in the epidural space in the spinal cord of a patient comprises percutaneously inserting an introducer having an epidural needle assembly extending through a cannula in the introducer between vertebrae in the patient's spine so that the leading tip of the epidural needle assembly and the introducer are adjacent the epidural space of the patient. The epidural needle assembly is withdrawn from the cannula of the introducer and the flexible member which is to be introduced to the epidural space is inserted through the cannula of the introducer until the flexible member is positioned in the epidural space. The introducer is then withdrawn from the patient leaving the flexible member in the epidural space.

In still another principal aspect of the present invention, the aforementioned epidural needle assembly comprises a needle having a cannula and an obturator. The obturator is positioned in the cannula when the introducer and epidural needle assembly are being inserted between the vertebrae and the obturator is thereafter withdrawn from the cannula of the needle.

In still another principal aspect of the present invention, the aforementioned methods include withdrawal of the introducer from the patient along the flexible member and, once it is withdrawn from the patient, the cannula of the introducer is split away from the flexible member.

In still another principal aspect of the present invention, in the aforementioned methods, the flexible member is a neural stimulator lead.

In still another principal aspect of the present invention, apparatus for the introduction of a flexible member into the epidural space in the spinal cord of a patient includes an introducer having an elongate cannula and an epidural needle assembly removably insertable in and through the cannula. The tip of the epidural needle assembly extends beyond an end of the elongate cannula, whereby the introducer and epidural needle assembly may be percutaneously inserted together between vertebrae in the patient's spine so that the tip of the epidural needle assembly and the end of the elongate cannula are adjacent the epidural space of the patient when the epidural needle assembly is fully inserted into the cannula of the introducer. A flexible member is also provided which is inserted in and through the cannula and into the epidural space when the epidural needle assembly has been removed from the cannula of the introducer.

In still another principal aspect of the present invention, the last mentioned epidural needle assembly comprises a needle having a cannula and an obturator removably inserted in the cannula of the needle.

In still another principal aspect of the present invention, the introducer in the aforementioned apparatus includes means for splitting the introducer away from the flexible member after the flexible member has been inserted in and through the cannula of the introducer.

In still another principal aspect of the present invention, the flexible member in the aforementioned apparatus is a neural stimulator lead.

These and other objects, features and advantages of the present invention will be clearly understood through a consideration of the following detailed description.

BRIEF DESCRIPTION OF THE DRAWINGS

In the course of this description, reference will be frequently made to the attached drawings in which:

FIG. 1 is an overall perspective view of a patient in which a neural stimulator has been installed and fixed in accordance with the principles of the present invention;

FIG. 2 is an exploded view showing an introducer and epidural needle assembly in accordance with the principles of the present invention;

FIG. 3 is an enlarged, partially broken and cross-sectioned view in perspective of the introducer and epidural needle assembly as shown in FIG. 2, but in assembled form;

FIG. 4 is an enlarged plan view of the introducer, as viewed substantially along line 4—4 of FIG. 2;

FIG. 5 is an enlarged plan view of the needle of the epidural needle assembly, as viewed substantially along line 5—5 of FIG. 2;

FIG. 6 is an enlarged plan view of the obturator of the epidural needle assembly, as viewed substantially along line 6—6 of FIG. 2;

FIG. 7 shows the epidural needle assembly and introducer being inserted between the vertebrae in the spine and adjacent to the epidural space of the patient;

FIG. 8 is a view similar to FIG. 7, but in which the introducer and epidural needle assembly has been inserted and the obturator of the epidural needle assembly is being withdrawn;

FIG. 9 is a view similar to FIG. 8, but in which the introducer is being finally positioned in the epidural space and the needle of the epidural needle assembly is being withdrawn from the introducer;

FIG. 10 is a view similar to FIG. 9, but in which the needle of the epidural needle assembly has been fully withdrawn from the introducer and the neural stimulator lead is being inserted into the introducer; and FIG. 11 is a view similar to FIG. 10, but in which the neural stimulator lead has been installed in the epidural space and the introducer is being withdrawn and split away from the lead.

DESCRIPTION OF THE PREFERRED EMBODIMENTS

The present invention is directed to a method and apparatus for installing a neural stimulator lead 10 in the epidural space 12 of the spine S of a patient, as shown in FIGS. 1 and 7-11.

The neural stimulator lead 10 is flexible and includes a suitable electrical conductor (not shown) which is preferably coated with a biologically compatible coating (not shown). The construction of such leads in this respect are conventional in the neural stimulator art and will not be described herein in detail. The lead also includes a suitable electrode 14, as shown in FIGS. 10 and 11, which may be located either at the tip of the lead or along its length. The electrode 14 will be positioned at the location in the epidural space at which stimulation is to occur and the lead and its electrode are fixed at that time. The other end of the lead 10 is terminated by a suitable electrical terminal 16 which may, for example, comprise a pin terminal 16 as shown in FIG. 11, which is molded or otherwise formed on the end of the lead. The terminal 16 may be employed to electrically connect the lead to an exterior conductor and exteriorly mounted stimulator, as in the case of a temporary lead installation, or the lead 10 may be electrically connected directly to a subcutaneously implanted stimulator 18, as shown in FIG. 1, in a permanent installation. The stimulator 18 generates electrical pulses or signals, as is known in the art, for stimulating one or more predetermined locations along the patient's spinal cord.

Preferred apparatus incorporating the principles of the present invention is shown in FIGS. 2-6.

As shown in FIGS. 2-4, an introducer 20 includes an elongate, tubular cannula 22 which is formed of a flexible, biologically compatible material, such as polyethylene. By way of example, the wall thickness of the cannula 22 may be approximately 0.01 inch, although heavier walls may be employed. The introducer cannula 22 need not be any larger in diameter than, for example, a 14 gauge Tuohy needle that was previously employed in the placement of neural stimulator leads.

The introducer 20 also preferably includes a pair of handles 24 and 26 at one end. Each of the handles 24 and 26 include a downwardly extending half tubular element 28 and 30, as best shown in FIG. 2. Half tubular elements 28 and 30 terminate in a half cylindrical recess 32 and 34 as shown in FIG. 3 to receive the upper end of the cannula 22. Elements 28 and 30 also have winged manipulating surfaces 36 and 38 at the upper end of each half tubular element 28 and 30, respectively, for manipulation by the physician installing the assembly of the present invention in the patient. The wings 36 and 38 preferably include roughened surfaces 40 thereon to facilitate such manipulation. The recesses 32 and 34 are positioned about the top of the cannula 22 and are affixed thereto in a suitable manner, such as by an adhesive, and such that the handles 24 and 26 are slightly separated from each other as shown in FIG. 2.

The half tubular elements 28 and 30 also preferably each include a semi-annular shoulder 41, as best seen in FIG. 4, with a bead 42 on each shoulder which acts as a stop for the epidural needle assembly upon full insertion of that assembly into the introducer.

The cannula 22 of introducer 20 preferably includes one or more weakened portions to facilitate splitting of the cannula 22 at the completion of the introduction of the lead, as will be described in detail to follow. As shown in FIGS. 2 and 3, such weakening may take the form of a score line 43 extending longitudinally over substantially the length of the cannula and upwardly between the handles 24 and 26 in the space therebetween. Although only a single score line is shown in FIGS. 2 and 3, it will be understood that a complementary score line may be included on the opposite side of the cannula 22 of the introducer.

An epidural needle assembly 44, as shown in FIG. 2, includes a needle 46 and an obturator 48. The needle assembly 44, as shown in FIG. 2, is a conventional Tuohy needle and is formed of a rigid, biologically compatible metal, such as stainless steel. The needle 46 comprises an elongate cannula 50 which is slightly longer than the cannula 22 of the introducer 20 so that when it is inserted in the introducer, as shown in FIG. 3, the open tip 52 of the cannula 50 projects slightly beyond the lower distal end 54 of the introducer. The projection of the open sharp tip 52 of the cannula 50 facilitates insertion of the epidural needle assembly 44 and introducer 20, as shown in FIGS. 7 and 8, and as will be described to follow.

The needle 46 may be somewhat smaller in diameter than the needles previously employed in the installation of neural stimulator leads because it is only used for insertion of itself and the introducer and is not employed in the actual installation of the neural stimulator lead as in the prior methods. Thus, where the Tuohy needles employed in the prior methods were typically 14 gauge; the needle 46 as employed in the present invention may be 17 gauge.

The needle 46 also includes an enlarged hub 56 to facilitate manipulation. The end of the hub 56 terminates in a seat 58 having a slightly raised annular seating area 60 upon which a downwardly facing seat 62 on the hub 64 of the obturator seats when the obturator 48 is fully inserted into the needle 46. The seat 58 and annular seating area 60 of the needle 46 also preferably include a notch 66 which receives a complementary lug 68 on the obturator hub 64, as shown in FIGS. 2 and 3, to prevent rotation of the obturator 48 when the obturator is fully inserted into the needle 46. The hub 56 of the needle 46 also includes a well 70, as shown in FIGS. 2 and 5, for receiving the obturator 48 when the obturator is inserted in the needle. The bottom of the well 70 communicates with the needle cannula 50.

The obturator 48, as previously mentioned, includes a hub 64 at one end thereof, and an elongate solid stylet 72 which fills and stops flow through the cannula 50 of the needle 46 when the obturator is inserted in the needle. The length of the stylet 72 is substantially equal to the length of the cannula 50 and the tip 74 of the stylet is shaped to fill the opening in the tip 52 of the needle 46 when the obturator 48 is fully inserted in the needle 46, as shown in FIG. 3.

A description of the preferred method of the present invention for introducing the neural stimulator lead 10 into the epidural space 12 of the spinal cord of the patient will now be described with particular reference to FIGS. 7–11.

Approximately a two inch midline incision (not shown) is made over the spinous process at the site at which the lead is to be inserted. The epidural needle assembly 44, comprising the needle 46 with the obturator 48 fully inserted therein, is inserted into the introducer 20 as shown in FIG. 3. The introducer 20 with the needle assembly 44 inserted therein is then percutaneously inserted at an oblique angle between two vertebrae V as shown in FIG. 7 until the leading tip 52 of the epidural needle assembly and the leading end 54 of the introducer are adjacent to and just enter the epidural space 12 at midline.

The obturator 48 is then withdrawn, as shown in FIG. 8, and the well 70 of the needle 46 is filled with a sterile saline solution. The introducer 20 and needle 46 are then slowly advanced together until the saline solution is drawn further into the needle, indicating that the needle has entered the epidural space.

At this point the needle 46 is withdrawn and removed from the introducer 20 while the introducer is simultaneously advanced about 0.5 cm., as shown in FIG. 9. Advancement of the relatively flexible introducer 20 causes the end 54 of the introducer to assume a slight angle, as shown in FIG. 9, to facilitate directing the lead 10 upon insertion of the lead into the introducer.

Following removal of the needle 46 from the introducer 20, the neural stimulator lead 10 is inserted into the introducer 20, as shown in FIG. 10, and the electrode 14 of the lead 10 is advanced through the cannula 22 of the introducer and along the epidural space 12 as shown in FIG. 11. Once the electrode 14 has been positioned in the epidural space at the site to be stimulated, the introducer 20 is withdrawn along the lead 10, as shown in FIG. 11, until the entire introducer has been withdrawn from the patient's body. At this point, each of the handles 24 and 26 are pulled laterally apart so as to cause the introducer 20 to split away from the lead 10, as shown in FIG. 11, along the weakened score line 43 before the introducer reaches the terminal 16.

It will be seen from the aforementioned description of the present invention, that a terminal 16 of larger diameter than the lead 10 may be molded directly to the lead at the time of manufacture and the introducer 20 may be easily and rapidly split away from the lead once the lead has been installed and fixed in its proper position without having to pull the introducer or any other element off over the end of the lead. Thus, the physician who is performing the installation of the lead does not have to crimp or otherwise attach a terminal to the lead following placement of the lead, thereby reducing the time involved in the installation procedure and the trauma to the patient and maximizing sterility and reliability of the installation.

The above described method of installation and fixation of the lead is of course greatly facilitated by utilizing X-ray fluoroscopy, ultrasonic imaging and other known techniques during the installation and fixation. Accordingly, the various elements of the apparatus of the present invention, such as the stimulator lead 10, the epidural needle assembly 44 and the introducer 20 are preferably formed of radiopaque material.

It will be understood that the embodiment of the present invention which has been described is merely illustrative of one of the applications of the principles of the present invention. Numerous modifications may be made by those skilled in the art without departing from the true spirit and scope of the invention.

What is claimed is:

1. A method of introducing a flexible member in the epidural space in the spinal column of a patient, comprising the steps of:
   percutaneously inserting an elongated flexible introducer having an epidural needle assembly extending through a cannula in the introducer between vertebrae in the patient's spine so that the leading tip of the epidural needle assembly and the introducer are adjacent said epidural space;
   withdrawing said epidural needle assembly from the cannula of said introducer;

inserting said flexible member through the cannula of said introducer until the flexible member is positioned in said epidural space;

withdrawing said introducer from the patient while leaving said flexible member in said epidural space; and splitting said flexible member along the elongate axis thereof following withdrawal of said introducer from the patient and removing said split introducer from around said flexible member.

2. The method of claim 1, comprising the additional steps of forming said epidural needle assembly by positioning an obturator in the cannula of an epidural needle, positioning said epidural needle assembly in said cannula of said introducer prior to said percutaneous insertion of said introducer, and withdrawing said obturator from said epidural needle following said percutaneous insertion of said introducer.

3. The method of claim 2, comprising the additional step of filling the cannula of the needle with a saline solution upon removal of the obturator.

4. The method of claim 3, comprising the additional step of advancing said introducer into the epidural space following filling said cannula of said epidural needle with said saline solution.

5. The method of claim 4, comprising the additional step of withdrawing said needle from said introducer while simultaneously advancing said introducer further into the epidural space such that said leading end of said introducer is caused to assume a slight angle.

6. The method of claim 2, wherein said step of forming said needle assembly comprises the step of positioning said obturator in the cannula of a Tuohy needle.

7. The method of claim 1, wherein said step of inserting said member comprises inserting a neural stimulator lead through the cannula of said introducer until said neural stimulator lead is positioned in the epidural space.

8. Apparatus for the introduction of a flexible member into the epidural space in the spinal column of a patient, comprising:

an elongated introducer comprising a flexible elongate cannula, said introducer being splittable along the elongate axis thereof; and an epidural needle assembly removably inserted in and through said cannula, the tip of said epidural needle assembly extending beyond an end of said elongate cannula, whereby said introducer and epidural needle assembly may be percutaneously inserted together between vertebrae in the patient's spine so that the tip of the epidural needle assembly and the end of said elongate cannula are adjacent the epidural space of the patient when the epidural needle assembly is fully inserted into the cannula of said introducer.

9. The apparatus of claim 8, wherein said epidural needle assembly comprises a needle having a cannula and an obturator removably inserted in the cannula of said needle.

10. The apparatus of claim 9, wherein the flexible member comprises a neural stimulator lead and said introducer is dimensioned to encircle said neural stimulator lead, said introducer further including means for splitting said introducer away from said neural stimulator lead after said lead has been inserted in and through said cannula of said introducer, said means for splitting including a weakened portion of said introducer extending longitudinally of said elongate cannula of said introducer, and a pair of handle means attached to the elongate cannula of said introducer adjacent the end thereof opposite the aforementioned end, said weakened portion extending between said handle means.

11. The method of claim 10, wherein said neural stimulator lead includes a terminal on an end thereof opposite the end which is positioned in the epidural space, said terminal being larger in cross-section than the lead, and said introducer may be withdrawn from the patient's body along said lead and split away from said lead before said introducer reaches said terminal.

12. The apparatus of claim 8, wherein said epidural needle assembly includes a Tuohy needle having a cannula, and an obturator removably inserted in said cannula of said Tuohy needle such that said cannula is filled by said obturator.

13. The apparatus of claim 8, wherein the flexible member is a neural stimulator lead and said introducer is dimensioned to receive said neural stimulator lead.

14. The apparatus of claim 8, wherein said introducer includes means for splitting said introducer along said elongate axis such that said introducer can be removed from said flexible member after said flexible member has been inserted in and through said cannula of said introducer.

15. The apparatus of claim 14, wherein said means for splitting includes a weakened portion of said introducer.

16. The apparatus of claim 15, wherein said weakened portion extends longitudinally of said elongate cannula of said introducer.

17. The apparatus of claim 15, wherein said weakened portion comprises a score line.

18. The apparatus of claim 17, wherein said means for splitting also includes a pair of handles attached to the elongate cannula of said introducer adjacent the end thereof opposite the aforementioned end, said score line extending between said handles.

19. The apparatus of claim 14, wherein said means for splitting includes a pair of handles attached to the elongate cannula of said introducer adjacent the end thereof opposite the aforementioned end.

20. The apparatus of claim 14, wherein said flexible member includes an end thereon opposite the end which is positioned in the epidural space and which is larger in cross-section than the flexible member, and said introducer may be withdrawn from the patient's body along said flexible member and split away from said flexible member before said introducer reaches said end.

* * * * *